United States Patent
Antonini et al.

(10) Patent No.: US 11,446,484 B2
(45) Date of Patent: Sep. 20, 2022

(54) DEVICE FOR ELECTROTHERAPY AND/OR ELECTROPHYSIOLOGY, KIT AND ASSEMBLY

(71) Applicant: WISE SRL, Milan (IT)

(72) Inventors: Alessandro Antonini, Milan (IT); Matteo Saini, Milan (IT); Laura Spreafico, Milan (IT); Sandro Ferrari, Milan (IT); Sergio Malorni, Milan (IT); Thomas Edward Parker, Milan (IT); Georgina Rose Koffler, Milan (IT); Caleb Luke Solomon, Milan (IT)

(73) Assignee: WISE SRL, Milan (IT)

( * ) Notice: Subject to any disclaimer, the term of this patent is extended or adjusted under 35 U.S.C. 154(b) by 31 days.

(21) Appl. No.: 16/840,101

(22) Filed: Apr. 3, 2020

(65) Prior Publication Data
US 2020/0316371 A1    Oct. 8, 2020

(30) Foreign Application Priority Data
Apr. 5, 2019    (IT) ...................... 102019000005268

(51) Int. Cl.
*A61N 1/05*    (2006.01)
*A61N 1/372*    (2006.01)

(52) U.S. Cl.
CPC ........... *A61N 1/0553* (2013.01); *A61N 1/372* (2013.01)

(58) Field of Classification Search
CPC ..... A61N 1/0553; A61N 1/372; A61N 1/0556
See application file for complete search history.

(56) References Cited

U.S. PATENT DOCUMENTS 6,319,241 B1    11/2001    King et al.
6,522,932 B1     2/2003    Kuzma et al.
(Continued)

FOREIGN PATENT DOCUMENTS

EP    1818074 A1    8/2007
EP    2553135 A1    2/2013
(Continued)

*Primary Examiner* — Alyssa M Alter
(74) *Attorney, Agent, or Firm* — Troutman Pepper Hamilton Sanders LLP (Rochester)

(57) ABSTRACT

Device (1) for electrotherapy and/or electrophysiology comprising at least one lead (2) having an elongated lead body extending along a longitudinal direction (X-X) and comprising a proximal end (3) and a distal end (4); and at least one paddle (5) having a paddle body comprising two opposite major surfaces (6, 7) defining a paddle thickness (33) there between; wherein said paddle (5) comprising at least one paddle electrode (8) having an exposed surface (9) designed to come into electrical contact with a living anatomy (10) inside a patient's body (11); said paddle (5) is suitable to modify the transverse encumber (12) thereof, so that to assume at least one transport configuration and at least one operative configuration, wherein the transverse encumber (12) of the paddle (5) when in said at least one transport configuration is less than the transverse encumber (12) of the same paddle (5) when in said at least one operative configuration; wherein said lead (2) comprising a connection portion (13) near the distal end (4) thereof; said connection portion (13) of the lead (2) comprises at least one arched electrically conductive surface (14); and said paddle (5) comprises at least one counter-connection portion (15) comprising at least one arched electrically conductive counter-surface (16) in direct contact with said at least one conductive surface (14) of the connection portion (13) of the lead (2), so that said at least one counter-connection portion (15) of the paddle (5) has a transversally arched shape defining a first concavity (R1) facing towards said connection portion (13) of the lead (2); said at least one conductive counter-surface (16) of the paddle (5) is in electric communication with said paddle electrode (8) through at least one conductive track (17) extending within the body of paddle (5) in such way that said proximal end (3) of the lead (2) is (Continued)

in electrical communication with said exposed surface (9) of the at least one paddle electrode (8).

12 Claims, 8 Drawing Sheets

(56) References Cited

U.S. PATENT DOCUMENTS

| | | |
|---|---|---|
| 6,676,346 B1 | 1/2004 | Frischmann |
| 6,714,822 B2 | 3/2004 | King et al. |
| 6,934,956 B1 | 8/2005 | Allen et al. |
| 2002/0024397 A1 | 2/2002 | Fujii et al. |
| 2005/0203602 A1 | 9/2005 | Wallace et al. |
| 2007/0027514 A1 | 2/2007 | Gerber |
| 2008/0140152 A1 | 6/2008 | Imran et al. |
| 2008/0311040 A1 | 12/2008 | Berry et al. |
| 2009/0270957 A1 | 10/2009 | Pianca et al. |
| 2012/0143296 A1* | 6/2012 | Pianca ................. A61N 1/0553 607/116 |
| 2014/0121674 A1 | 5/2014 | Staunton |
| 2014/0343564 A1 | 11/2014 | Feler et al. |

FOREIGN PATENT DOCUMENTS

| | | |
|---|---|---|
| WO | 2003015263 A1 | 2/2003 |
| WO | 2011121017 A1 | 10/2011 |
| WO | 2017203441 A1 | 11/2017 |

\* cited by examiner

DEVICE FOR ELECTROTHERAPY AND/OR ELECTROPHYSIOLOGY, KIT AND ASSEMBLY

This application claims the priority benefit of Italy Provisional Patent Application No. 102019000005268, filed on Apr. 5, 2019, which is hereby incorporated by reference in its entirety.

DESCRIPTION

Field of Invention

An object of the present invention is a device for electrotherapy and/or electrophysiology.

The present invention also relates to a stimulator for electrotherapy comprising such a device as described herein.

Moreover, the present invention relates to a recorder for electrophysiology comprising such a device as described herein.

The present invention also relates to a kit comprising said device.

State of the Art

Minimally invasive surgical procedures for the delivery of an implantable device in the human body are generally known in the art. For example, it is known to use interventional catheters for accessing the target living anatomy through, for example, a venous port.

It is also known to deliver deployable implantable devices, able to reduce their radial size when in the transport configuration to fit the lumen of an interventional catheter and eventually able to increase their radial size when the implantation site is reached.

These known implantable devices are generally controlled by control wires extending all way through the catheter longitudinal lumen in such way to allow an operator, typically a surgeon, to control the implantable device deployment from a control station, for example a catheter handle, located outside the patient's body.

Shape memory materials, for example shape memory alloys, like nitinol and the like and/or for example shape-memory cross-linked polymers, are also generally used for biomedical implants and have the unique capability to restore their original shape when subject to suitable thermal stress. For example, self-expanding stent grafts and other radially expansible implantable structure are typically made of nitinol, in order to have the property of self-expanding when implanted in a living anatomy due to the temperature increase within the patient's body. Shape-memory cross-linked polymers typically achieve the shape memory effect thanks to melting transition from a hard to a soft phase, substantially like a glass material.

Super-elastic materials, commonly referred to as pseudo-elastic materials, are also known in the art and exhibit the unique capability to undergo to extremely large elastic reversible deformation without for that reason requiring a thermal activation to achieve its original shape. In the technical field of electrophysiology, it is known to provide implantable electrodes for detecting the electrical activity of a living anatomy. For example, the electrical activity of the brain may be detected by means of needle electrodes inserted in the patient's scalp. A control unit comprising a recording device is typically associated to the implantable electrodes for recording and filtering the detected signal, for example the electro-corticography signal.

Implantable electrodes for electrotherapy are also known in the art. For example, artificial cardiac pacing is commonly achieved by means of implantation of an active device able to transfer a stimulation pattern to the contractile tissue of the heart in order to control the heart rate.

In the technical field of neuromodulation, implantable electrodes are used to induce a controlled alteration of the function of a nervous tissue by means of applying a specific electric and/or magnetic stimulation patterns. Neuromodulation treatments also include applications in medication-resistant epilepsy, chronic head pain conditions and functional therapy ranging from bladder and bowel or respiratory control to improvement of sensory deficits, such as hearing (cochlear implants and auditory brainstem implants) and vision (retinal implants). For example, peripheral nerve stimulation of the occipital nerves aims to relief chronic migraine pain.

Moreover, the technical field of brain-computer interface uses implantable electrodes for providing a two-way direct communication between a brain and a device, mainly for neuroprosthetics, in order to restore damaged movement, sight and/or hearing. The two-way communication requires some implantable electrodes to act as stimulation electrodes for transmitting electrical stimuli and some others as recording electrodes for sensing the electrical activity of the target living anatomy. Therefore, a plurality of such electrodes are usually arranged in an array form.

In addition, in the field of cardiac resynchronization therapy implantable electrodes are employed. Typically, these electrodes comprises stimulation electrodes to transfer the electrical impulses to the heart as well as recording electrodes to detect information about the electrical state and activity of the heart.

As the need is felt to introduce an implantable electrode within a target living anatomy with the purpose of electrical interaction with the tissue of the target living anatomy, it is desirable that the electrode is implanted through a percutaneous access that necessarily limits the maximum size of the electrode.

For example, it is generally known to implant electrodes for spinal cord stimulation (SCS) aiming to relieve of chronic pain. These stimulation electrodes are inserted in the epidural space, which is a channel extending along the vertebral foramen of the spinal column and behind the spinal cord in the sagittal plane of the patient's body.

It is widely known in the art to provide deployable electrodes for living tissue stimulation that are associated to the distal end of a catheter shaft for percutaneous delivery to a target living tissue.

Deployable electrodes usually comprises springs for biasing the body of the deployable structure thereof in deployment.

Deployable electrodes are generally able to increase the transversal size thereof when unconstrained by the delivery catheter or a part thereof.

For example, document US-2008-140152 shows a transversally foldable paddle electrode having body of the implant structure made of a thin film of flexible circuitry. This solution allows to deploy the paddle after having reached the target tissue. However, this solution results in poor manoeuvrability when the paddle electrode is unconstrained by the delivery catheter or a part thereof, due its high flexibility.

Other known examples of deployable electrodes are shown in documents US-2005-0203602, US-2009-0270957, EP-1818074, U.S. Pat. Nos. 6,319,241, 6,522,932, US-2014-0121674, US-8934956, US-2014-0343564, PCT-US02-24397, U.S. Pat. No. 8,676,346 and US-2007-0027514.

Documents WO-20111-121017 and EP-2553135, in the name of the same Applicant, disclose a technique for production of electrically functionalized stretchable articles, by means of the burial of nano-metric neutral particles beneath the free surface of an elastic flexible substrate and within the core of the substrate.

Moreover, document WO-2017-203441, in the name of the same Applicant, describes a technique to connect an intrinsically stretchable functionalized conductive polymer to a rigid electrical conductor.

Document U.S. Pat. No. 6,714,822 shows a rigid lead tip having a plurality of flexible paddle electrodes transversally extending therefrom. During transport within a delivery catheter, said flexible paddle electrodes are folded around the rigid tip. This solution allows to deploy the paddle electrodes through a pivoting movement of the entire lead about its longitudinal axis.

However, the proposed deployment strategy generates torque stress along the lead during deployment. Moreover, when in transport configuration within a delivery catheter constraining sheath, the paddle electrodes comprising metal conductive lines cannot bend beyond a certain curvature radius without compromise the structural integrity of the metal, therefore forcing to have void volumes inside the sheath. Thus, the delivery sheath diameter over the paddle width ratio is high.

Therefore, it is felt the need to provide a deployable electrode having improved manoeuvrability both when in transport configuration and in the operative configuration when compared to known solutions, and at the same time having lower delivery system size over paddle width ratio.

Solution

It is a scope of the present invention to overcome the drawbacks cited with reference to the prior art and to provide a solution able to meet the above-mentioned needs. This and other scopes are achieved by means of a device for electrotherapy and/or electrophysiology comprising: at least one lead (2) having an elongated lead body extending along a longitudinal direction (X-X) and comprising a proximal end (3) and a distal end (4); and at least one paddle (5) having a paddle body comprising two opposite major surfaces (6, 7) defining a paddle thickness (33) there between. The paddle (5) comprises at least one paddle electrode (8) having an exposed surface (9) designed to come into electrical contact with a living anatomy (10) inside a patient's body (11). The paddle (5) is suitable to modify the transverse encumber (12) thereof, so that to assume at least one transport configuration and at least one operative configuration, wherein the transverse encumber (12) of the paddle (5) when in said at least one transport configuration is less than the transverse encumber (12) of the same paddle (5) when in said at least one operative configuration. The lead (2) of the device comprises a connection portion (13) near the distal end (4) thereof; and the device is characterised in that said connection portion (13) of the lead (2) comprises at least one arched electrically conductive surface (14); and said paddle (5) comprises at least one counter-connection portion (15) comprising at least one arched electrically conductive counter-surface (16) in direct contact with said at least one conductive surface (14) of the connection portion (13) of the lead (2), so that said at least one counter-connection portion (15) of the paddle (5) has a transversally arched shape defining a first concavity (R1) facing towards said connection portion (13) of the lead (2). The at least one conductive counter-surface (16) of the paddle (5) is in electric communication with said paddle electrode (8) through at least one conductive track (17) extending within the body of paddle (5) in such way that said proximal end (3) of the lead (2) is in electrical communication with said exposed surface (9) of the at least one paddle electrode (8).

Another aspect of the present disclosure is directed to a kit. This kit (30) comprises at least one device (1) according to any one of the embodiments and claims described herein and a percutaneous delivery system (27), where the percutaneous delivery system (27) comprises at least one hollow body (28), wherein said hollow body (28) houses said at least one device (1) when in transport configuration.

Another aspect of the present disclosure is directed to an assembly (51). This assembly (51) comprises at least one device (1) according to any embodiment or claims described herein and at least one control unit (36), wherein said assembly (51) is a stimulator for electrotherapy and/or a recorder for electrophysiology.

Advantageous embodiments of the device, kit, and assembly are described herein and set forth herein and in the dependent claims.

Thanks to the proposed solutions, it is provided a device able to fit the size of the inner cavity of a hollow body for the delivery, and at the same time able to provide fine-tuned localization of at least one electrode within a living anatomy.

Thanks to the proposed solutions, it is provided a device able to combine the features of directional and localized stimulation with the capability of percutaneous implantation in a living anatomy.

BRIEF DESCRIPTION OF THE FIGURES

Further characteristics and advantages of the invention will appear from the description reported below of preferred embodiments, which are given as examples and are not meant to be limiting, which makes reference to the attached figures, wherein.

DETAILED DESCRIPTION

Figure 1:
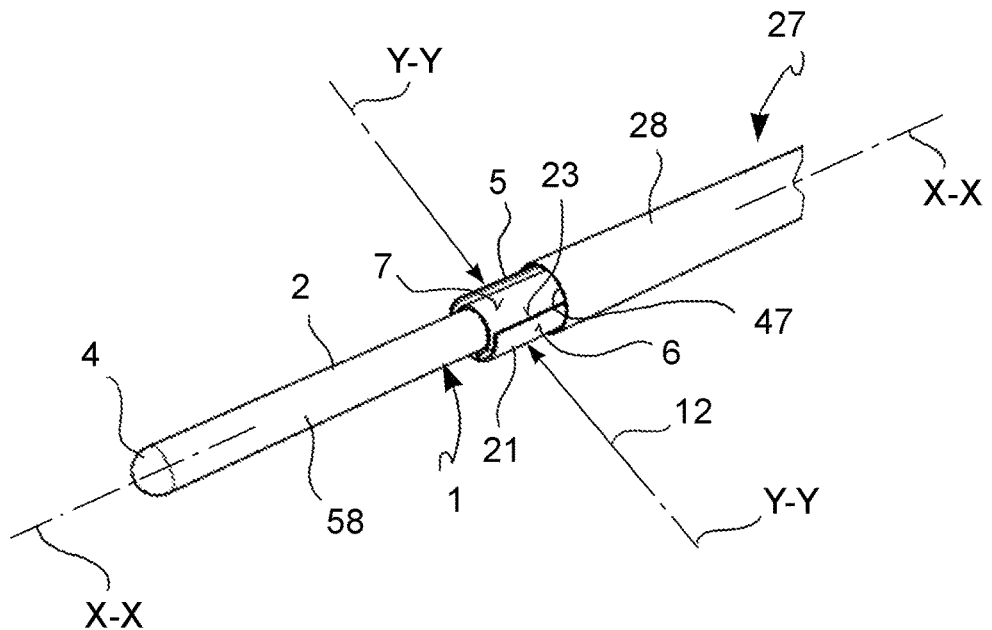
FIG. 1 is an axonometric view of a device, according to an embodiment, when in a transport configuration.
Figure 2:
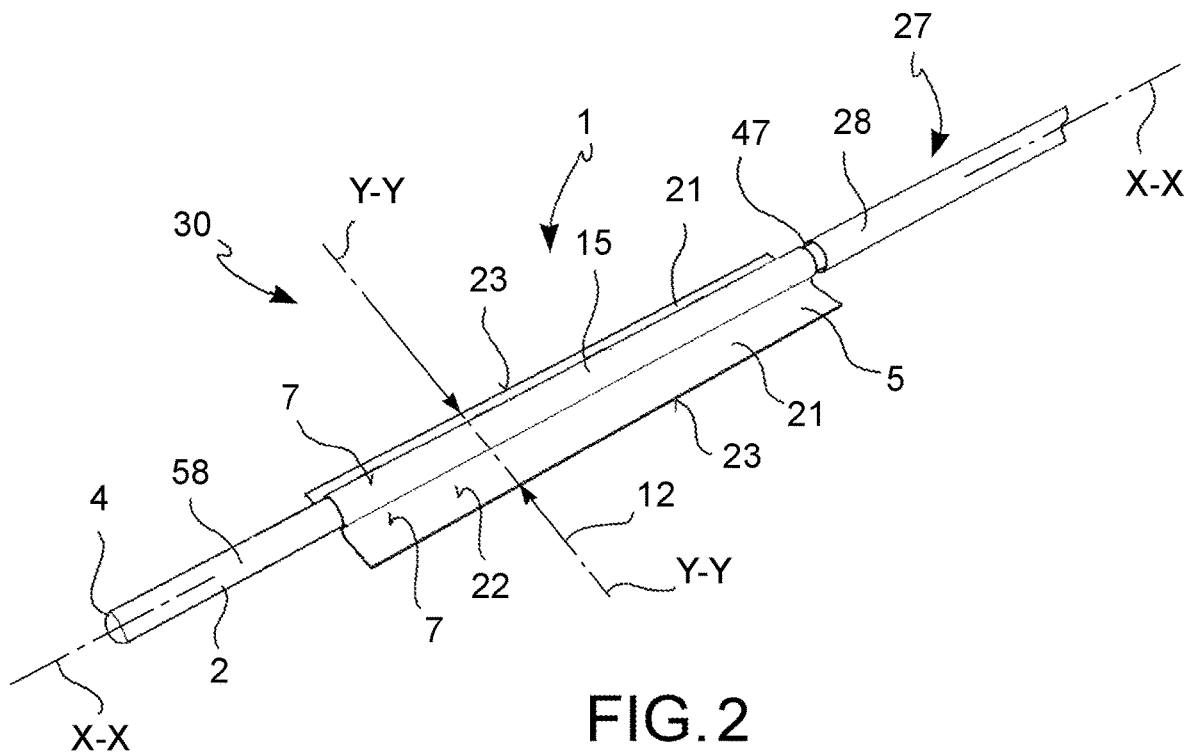
FIG. 2 is an axonometric view of a device, according to an embodiment, when in an operative configuration.
Figure 3:
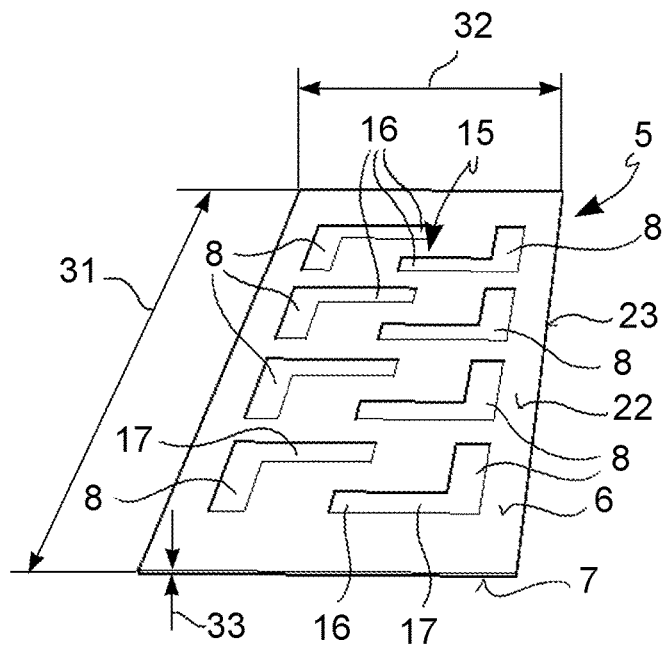
FIG. 3 is a perspective view of a paddle, according to an embodiment of the device as described herein.
Figure 4:
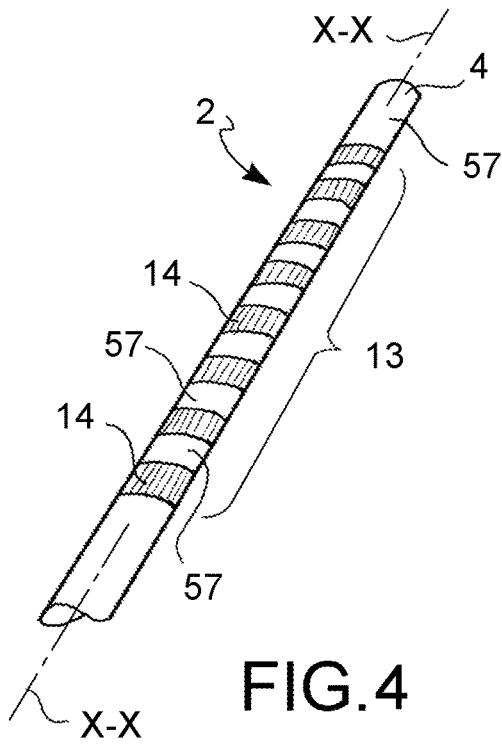
FIG. 4 is a perspective view of a lead, according to an embodiment of the device as described herein.
Figure 5:
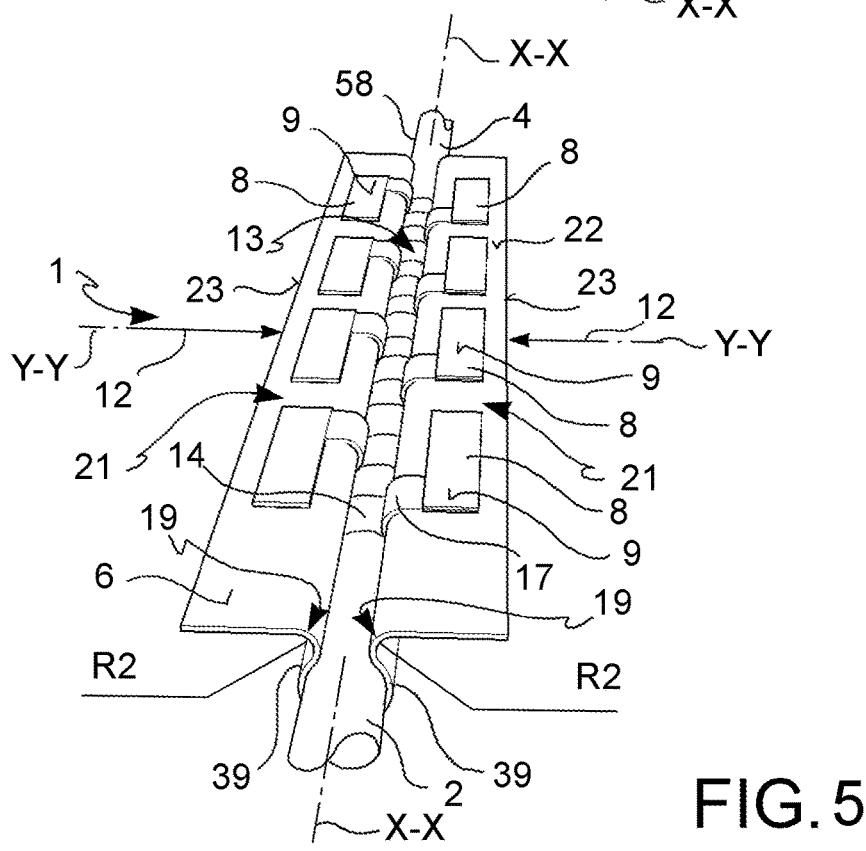
FIG. 5 is a perspective view of a device comprising the paddle of FIG. 3 and the lead of FIG. 4.
Figure 6:
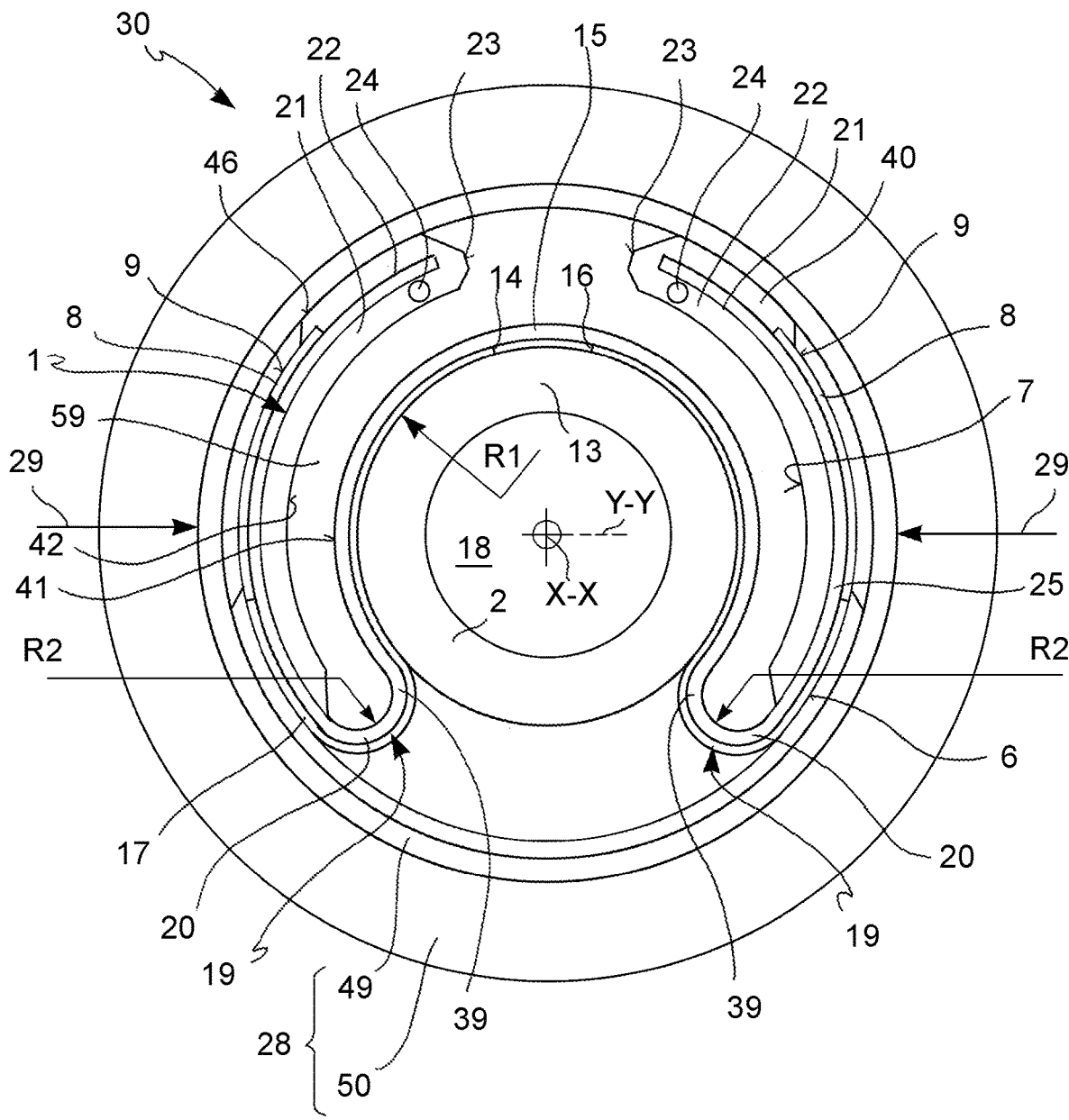
FIG. 6 shows a cross-section of a kit comprising a device, according to an embodiment, and a portion of a delivery system.
Figure 7:
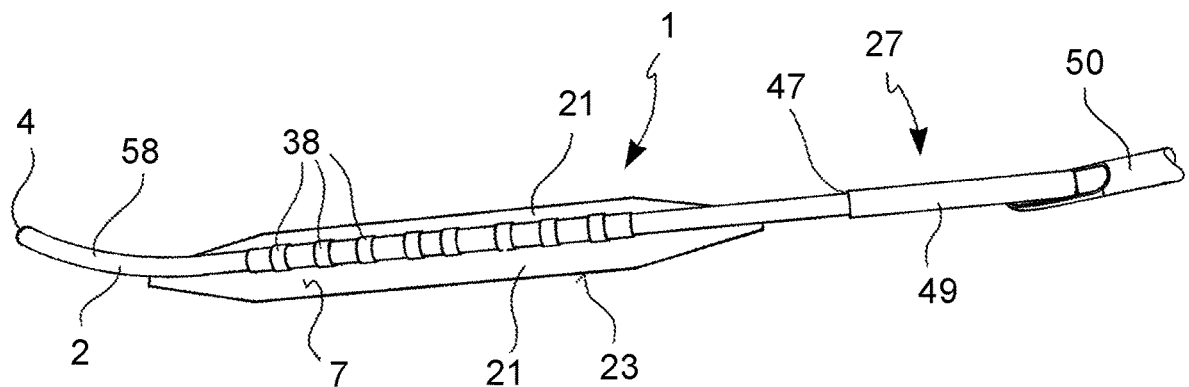
FIG. 7 is an axonometric view of a kit comprising a device, according to an embodiment, and a portion of delivery system.
Figure 8:
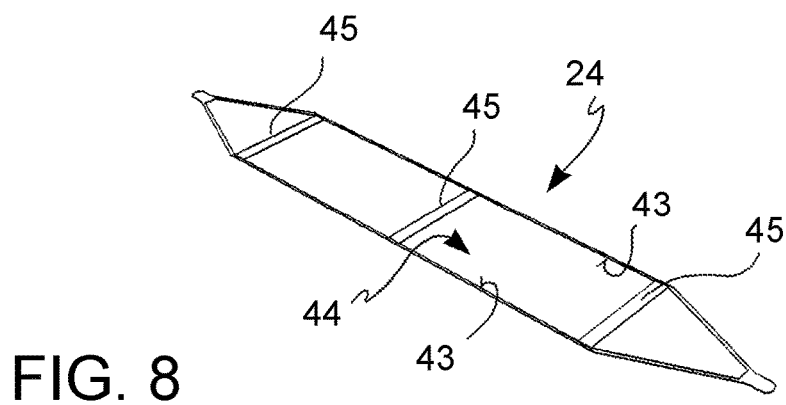
FIG. 8 shows a perspective view of a biasing device, according to some embodiments of the device described herein.
Figure 9:
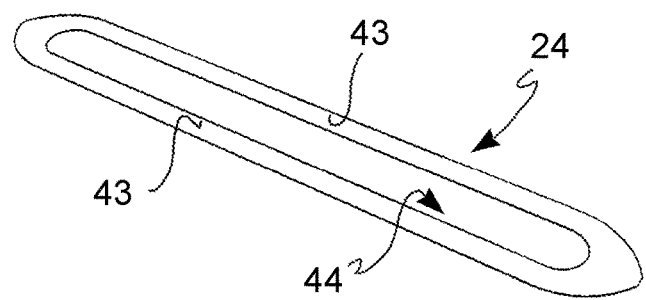
FIG. 9 shows a perspective view of a biasing device, according to some embodiments of the device described herein.
Figure 10:
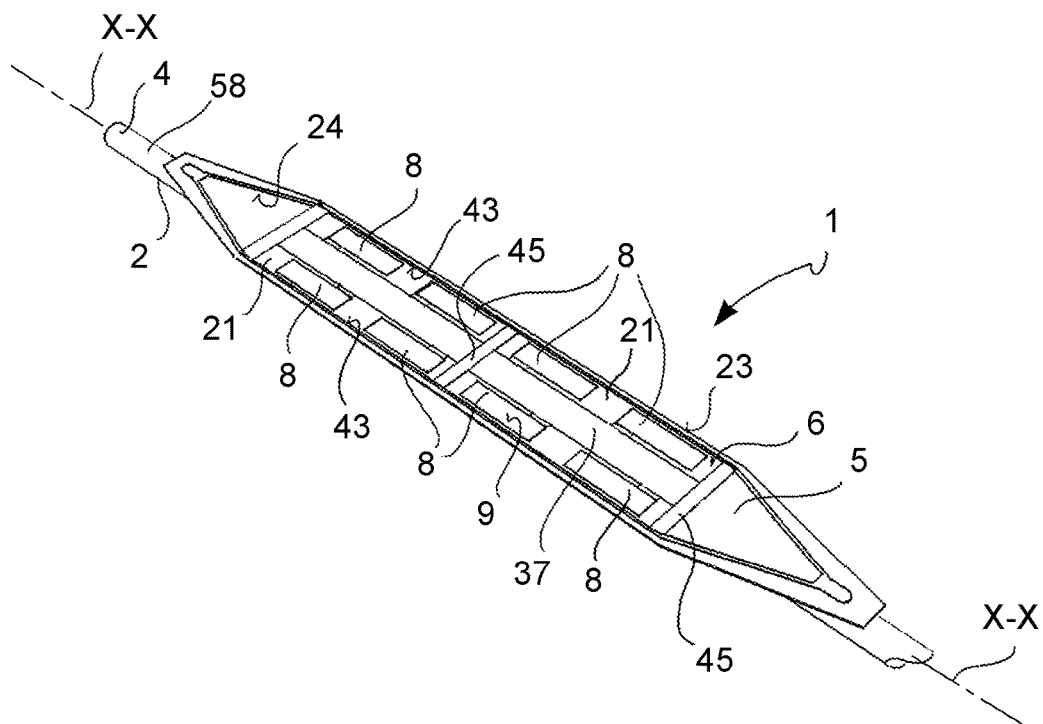
FIG. 10 shows a perspective view of a device, according to an embodiment described herein.
Figure 11:
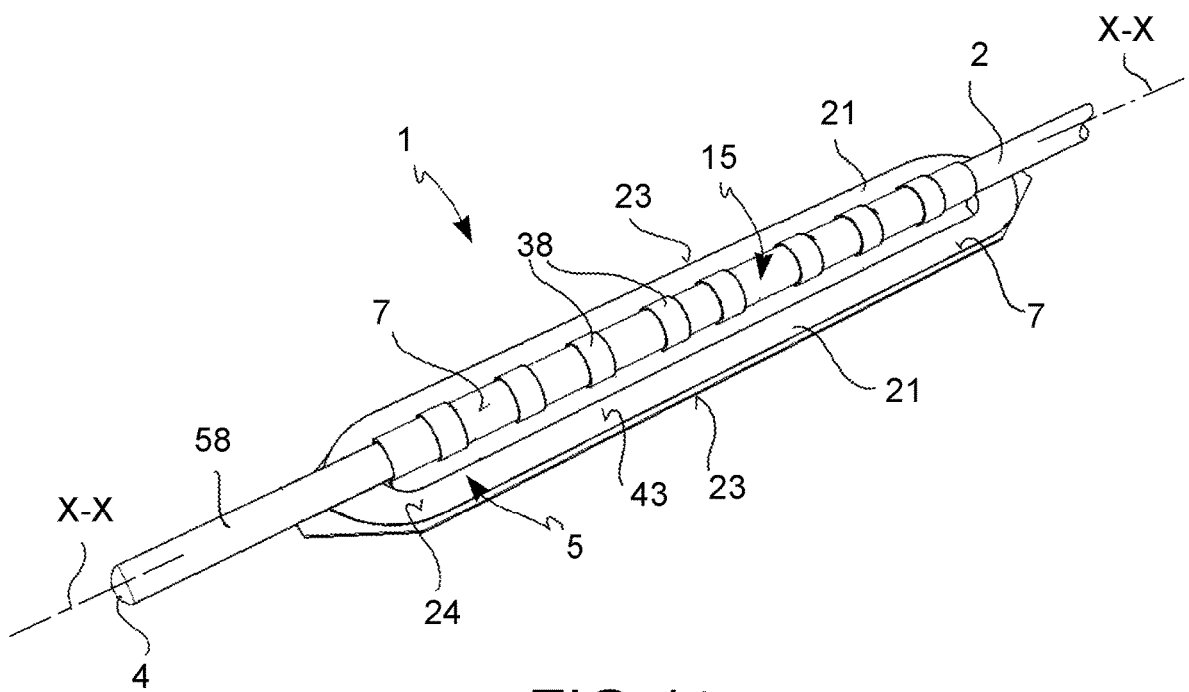
FIG. 11 shows a perspective view of a device, according to an embodiment as described herein.
Figure 12:
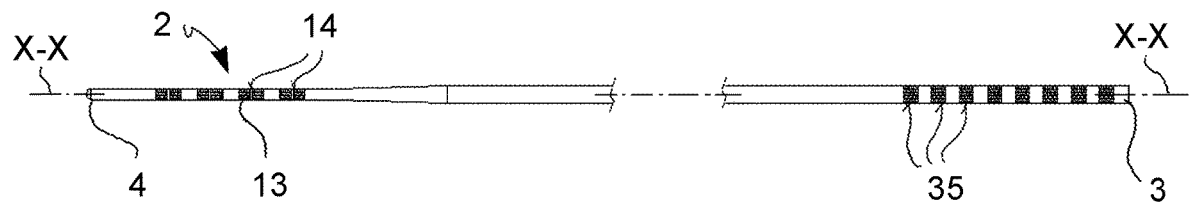
FIG. 12 shows an elevation view of a lead of an implantable electrode assembly, according to an embodiment as described herein.
Figure 13:
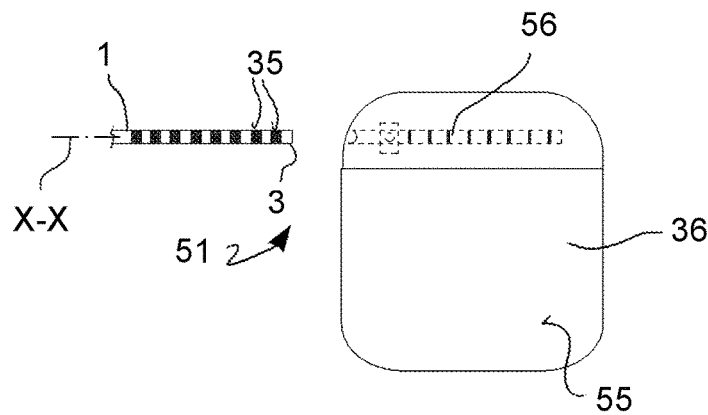
FIG. 13 shows an elevation view of an assembly, according to some embodiments as described herein, comprising a portion of lead and a control device.
Figure 14:
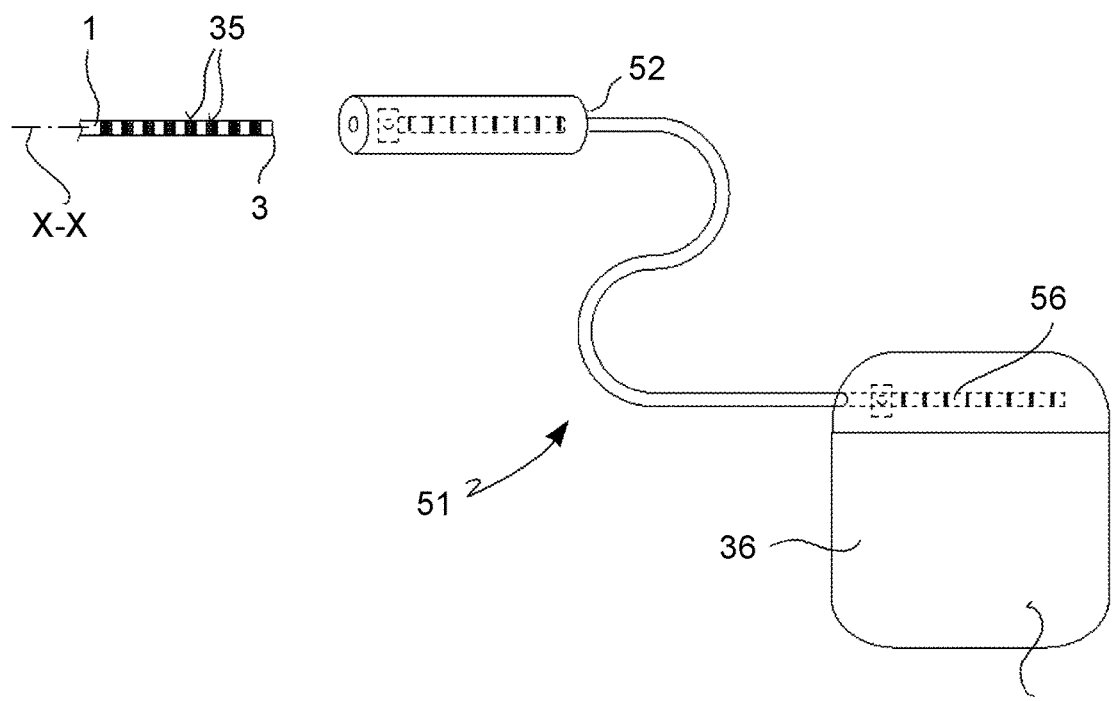
FIG. 14 shows an elevation view of an assembly, according to some embodiments as described herein, comprising a portion of lead and a control device.

A detailed description of the invention will now be provided with specific reference to Figures illustrating various exemplary embodiments and various structures/components of those exemplary embodiments. It will be appreciated that like structures/components are provided with like reference designations.

According to a general embodiment, a device 1 comprises at least one lead 2 and at least one paddle 5.

Said device 1 is suitable for application in electrotherapy.

Said device 1 is suitable for application in electrophysiology.

Preferably, said device 1 is an implantable device 1. Preferably, the term "implantable" means that the device 1 is designed to be implanted long term, preferably permanently, within a living anatomy 10 inside a patient body 11. Preferably, the term "implantable" also means that the device 1 is designed to be implanted temporary for example during surgery within a living anatomy 10 inside a patient body 11.

A device 1 according to the present invention is suitable for electrotherapy applications such as: pain reduction, implanted muscle stimulation, treatment of neuromuscular dysfunctions, tissue repair, treatment of urine and fecal incontinence, treatment of masculine erectile dysfunctions, treatment of edema, lymphatic drainage, peripheral nerve stimulation. The implantable electrode assembly 1 according to the present invention is particularly suitable for, although not univocally intended to, spinal cord stimulation.

A device 1 according to the present invention is suitable for electrophysiology applications such as: peripheral nerve recording, cardiac wall recording, electro-corticography, electroencephalography, electromyography.

A device 1 according to the present invention is also suitable for intra-operatory procedures, to support surgery.

Said at least one lead 2 has an elongated lead body extending along a longitudinal direction X-X and comprising a proximal end 3 and a distal end 4.

According to an embodiment, said longitudinal direction X-X is coincident with the axis of longitudinal development of the lead 2 elongated body.

According to an embodiment, a transversal direction Y-Y is defined orthogonal to said longitudinal direction X-X.

According to an embodiment, a cylindrical set of coordinates is defined, comprising said longitudinal direction X-X, a radial direction Y-Y orthogonal to said longitudinal direction X-X and incident with said longitudinal direction X-X, and a circumferential direction, orthogonal both to said longitudinal direction X-X and to said radial direction Y-Y.

According to an embodiment, at least the distal end 4 of the lead 2 comprises a substantially cylindrical body, preferably having a rounded cross-section around said longitudinal direction X-X.

According to an embodiment, at least the distal end 4 of the lead 2 is tapered, to reduce the transversal or radial encumber of the device 1.

According to an embodiment, the proximal end 3 of the lead 2 comprises electrical contacts 35 for electrically connect with a control device 36. For example, said control device 36 comprises a pulse generator.

Said at least one paddle 5 has a paddle body comprising two opposite major surfaces 6, 7 defining a paddle thickness 33 there between. Preferably, said two opposite major surfaces 6, 7 of the paddle 5 face opposite one another. Preferably, each of said two opposite major surfaces 6, 7 of the paddle 5 comprises a major surface longitudinal size 31 extending along said longitudinal direction X-X and a major surface width 32 transversal to said major surface longitudinal size 31. Preferably, the paddle thickness 33 is a fraction of each the major surface longitudinal size 31 and/or width 32. For example, the paddle 5 is in form of a film or the like.

Said paddle 5 comprises at least one paddle electrode 8 having an exposed surface 9 designed to come into electrical contact with a living anatomy 10 inside a patient's body 11. For example, said living anatomy may comprise a living tissue and/or organ and/or a body fluid.

Thanks to the provision of said at least one electrode 8 said device 1 may provide electrical stimulation to said living anatomy 10.

Thanks to the provision of said at least one electrode 8 said device 1 may record electrical activity of a living anatomy 10.

Said exposed surface 9 of the at least one electrode 8 acts as electrical termination of the device 1.

According to an embodiment, said at least one paddle electrode 8 comprises a exposed surface 9 that functionally emerges from said first major surface 6 of the paddle 5. In other words, said exposed surface 9 of said at least one electrode 8 forms together with said first major surface 6 of the paddle body 5 the outer surface of the paddle 5, that is to say the boundary of the paddle 5 volume.

The terminology "exposed surface 9 that functionally emerges from said first major surface 6" means that the paddle 5 exhibits said exposed surface 9 of the paddle electrode 8, and the exposed surface 9 does not necessarily protrude from the first major surface 6, although according to an embodiment the exposed surface 9 does protrude from said first major surface 6.

According to an embodiment, the terminology "exposed surface 9 that functionally emerges from said first major surface 6" indicates also the case wherein said at least one electrode 8 covers the entire first major surface 6 of the paddle 5 forming an exposed surface 9, as well as the case wherein said at least one electrode 8 covers the entire first major surface 6 of a paddle half-body, for example a paddle wing 21.

Said paddle 5 is suitable to modify the transverse encumber 12 thereof, so that to assume at least one transport configuration and at least one operative configuration, wherein the transverse encumber 12 of the paddle 5 when in said at least one transport configuration is less than the transverse encumber 12 of the same paddle 5 when in said at least one operative configuration. In other words, the radial encumber 12 of the paddle 5 when in said at least one transport configuration is less than the radial encumber 12 of the same paddle 5 when in said at least one operative configuration.

According to an embodiment, said paddle 5 is deployable.

According to an embodiment, said paddle 5 is self-expansible.

According to an embodiment, said paddle 5 is self-expanding.

Said lead 2 comprises a connection portion 13 near the distal end 4 thereof.

Preferably, said connection portion 13 of the lead 2 is unsuitable to modify the transverse encumber thereof. In this way, said connection portion 13 of the lead 2 is substantially rigid in the radial direction and unsuitable to reduce its radial dimension under an external loading action.

According to an embodiment, said connection portion 13 of the lead 2 radially delimiting a longitudinal cavity 18 for hosting a guiding stylet. In this way, the elongated body of at least the portion near the distal end 4 of the lead 2 is longitudinally hollow. Preferably, the distal end 4 of the lead 2 longitudinally closes said longitudinal cavity 18. The provision of said longitudinal cavity 18 for receiving a steerable stylet improves the manoeuvrability of the device 1 inside the patient body 11.

Advantageously, said connection portion 13 of the lead 2 comprises at least one arched electrically conductive surface 14. According to a preferred embodiment, said connection portion 13 of the lead 2 comprises electrically insulant portions 57 comprising each at least one electrically insulant surface in between of two subsequent arched conductive surfaces 14 of the of the connection portion 13 of the lead 2.

With further advantage, said paddle 5 comprises at least one counter-connection portion 15 comprising at least one arched electrically conductive counter-surface 16 in direct contact with said at least one conductive surface 14 of the connection portion 13 of the lead 2, so that said at least one counter-connection portion 15 of the paddle 5 has a transversally arched shape defining a first concavity R1 facing towards said connection portion 13 of the lead 2.

Said at least one conductive counter-surface 16 of the paddle 5 is in electric communication with said paddle electrode 8 through at least one conductive track 17 extending within the body of paddle 5 in such way that said proximal end 3 of the lead 2 is in electrical communication with said exposed surface 9 of the at least one paddle electrode 8.

The provision of such connection portion 13 of the lead 2 and said counter-connection portion 15 of the paddle 5 it is possible to have a larger electrically conductive contact surface area between paddle 5 and lead 2 with respect to known solutions.

Thanks to such a device 1, it is possible to provide localized and directional stimulation to a living anatomy 10 and at the same time it is possible to deliver the device 1 percutaneously inside a patient body 11, by means a mininavasive surgery.

Moreover, thanks to such a device 1, it is possible to provide localized and directional recording of the electrical activity of a living anatomy 10 and at the same time it is possible to deliver the device 1 percutaneously inside a patient body 11, by means a mininavasive surgery.

Preferably, thanks to said connection portion of the lead cooperating to said counter-connection portion of the paddle, no welding points are required between paddle and lead, without for this reason weakening the adhesion, thus reducing the radial or transversal encumber of the device 1 when in transport configuration.

According to a preferred embodiment, said connection portion 13 of the lead 2 also forms a mechanical connection with said counter-connection portion 15 of the paddle 5. In this way, said connection portion 13 of the lead 2 also forms an electrical and mechanical connection with said counter-connection portion 15 of the paddle 5.

According to an embodiment, fixing means 37, 38 are provided mechanically connecting said connection portion 13 of the lead 2 and said counter-connection portion 15 of the paddle 5.

According to an embodiment, glue 37 is provided mechanically connecting said connection portion 13 of the lead 2 and said counter-connection portion 15 of the paddle 5. Preferably, said glue 37 is electrically insulant. Preferably, said glue 37 is placed between electrically insulant surfaces.

According to an embodiment, a plurality of clips 38 is provided mechanically connecting said connection portion 13 of the lead 2 and said counter-connection portion 15 of the paddle 5.

According to a preferred embodiment, said plurality of clips 38 apply compressive force on the electrically conductive surface to create electrical contact.

According to a preferred embodiment, said connection portion 13 of the lead 2 has a cylindrical shape and said counter-connection portion 15 of the paddle 5 embraces at least a portion of said cylindrical connection portion 13 of the lead 2. In this way, a cross-section of the device 1, taken in a plane orthogonal to said longitudinal direction X-X, comprises a rounded connection portion 13 of the lead 2 embraced for a predetermined first angular portion by said counter-connection portion 15 of the paddle 5. Preferably, a second angular portion of said cross-section of the connection portion 13 of the lead 2 is free from contact with said paddle 5. According to an embodiment, glue 37 is provided around said second angular portion of the connection portion 13 of the lead 2.

According to a preferred embodiment, said paddle 5 comprises at least one paddle fold 19 defining at least one transversally folded portion 20 of the paddle 5 comprising said at least one paddle fold 19. Preferably, said at least one transversally folded portion 20 of the paddle 5 is disjoined from said arched counter-connection portion 15 of the same paddle 5. In this way, the paddle 5 comprises at least two different arched portions.

According to a preferred embodiment, said at least one transversally folded portion 20 of the paddle 5 defines a second concavity R2 opposite to said first concavity R1. In this way, a change of concavity is defined along the body of the paddle 5. In this way, the paddle 5 comprises at least one flex 39 in between said at least one paddle fold 19 and said at least one arched connection portion 15 of the paddle 5.

According to a preferred embodiment, said paddle 5 comprises at least one paddle transversal edge 22 delimiting the width of said major surfaces 6, 7, and wherein said at least one paddle fold 19 is located between said counter-connection portion 15 and said transversal edge 22 of the paddle 5, defining a paddle wing 21 comprising a free end 23 and at least a portion of said at least one paddle electrode 8. Preferably, said paddle wing 21 is wider than said counter-connection portion 15 of the paddle 5.

According to a preferred embodiment, said at least one paddle fold 19 defining at least one transversally folded portion 20 of the paddle 5 is provided both when the paddle 5 is in the transport configuration and when the paddle 5 is in the operative configuration.

According to a preferred embodiment, said paddle 5 comprises two opposite paddle folds 19 opposite with respect to said counter-connection portion 15 of the paddle 5 defining at least two opposite paddle wings 21 each having a free end 23.

According to an embodiment, when in said at least one paddle wing 21 is able to change its orientation in respect of said lead 2, in order to bring said exposed surface 9 of said at least one paddle electrode 8 at various distances from the lead 2. Furthermore, said at least one paddle wing 21 able to change its orientation in respect of said lead 2, allows to align the exposed surface 9 of the at least paddle electrode 8 to lean against a target anatomic part.

Preferably, said at least one paddle wing 21 is flexible at least in the transverse direction, so that is able to adhere against a curved target anatomic part.

Preferably, when in transport configuration, said at least two opposite paddle wings 21 are folded in such way that a first portion 41 of one of said major surfaces 6 or 7 of the paddle 5 faces in the transversal or radial direction a second portion 42 of the same major surface 6 or 7 of the paddle 5.

When the wings 21 of the paddle 5 are exactly in number of two and opposite with respect of said counter-connection portion 15 of the paddle 5, the cross-section of the device 1 assume a "omega"-like shape, in other words a "Ω"-like shape, where the wings 21 are the flat segment of the omega and the counter-connection portion 15 of the paddle 5 is the arched bridge of the omega.

According to an embodiment, said at least one paddle wing 21 comprises an array of paddle electrodes 8. Said array of paddle electrodes 8 may be unipolar or bipolar. The paddle electrodes 8 of said array of paddle electrodes 8 may be arranged substantially aligned along the longitudinal direction X-X and/or may be arranged offset one another.

According to a preferred embodiment, said device 1 comprises at least one biasing device 24 biasing said paddle 5 towards said operative configuration. In this way, said at least one biasing device 24 exerts a biasing action onto said paddle 5 towards the operative configuration.

Not necessarily said biasing action is an elastic biasing action, although according to a preferred embodiment it is.

Preferably, said biasing device 24 comprises at least one elongated element 43 forming a closed path, said elongated element 43 being arranged near the transversal edges of the paddle 5. Preferably, said elongated element 43 extends along the free edge 23 of the paddle wing 21. According to an embodiment, said elongated element 43 delimits at least one through hole 44. According to an embodiment, said biasing device 24 comprises one or more stiffening elements 45 connected to said at least one elongated element 43. Preferably, said one or more stiffening elements 45 are beams extending transversally.

According to an embodiment, said at least one biasing device 24 comprises at least one elastic element and/or a super-elastic material.

Preferably, the terminology "pseudo-elastic" and "super-elastic" refer to "pseudo-elasticity" and "super-elasticity", which in turn refer to elastic reversible response caused by a phase transformation between the austenitic and martensitic phases. Preferably, "pseudo-elasticity" and "super-elasticity" are substantially isotherm processes.

The term "elastic device" used herein also encompasses elements having pseudo-elastic or super-elastic behavior.

The stiffness of the elastic device can be chosen in order to overcome the resistance of the living tissue inside the patient body.

According to an embodiment, said at least one biasing device 24 comprises at least one wire spring.

According to an embodiment, said at least one biasing device 24 comprises at least one leaf spring.

According to an embodiment, said at least one biasing device 24 comprises at least one coil spring.

According to an embodiment, said at least one biasing device 24 comprises at least one shape memory element made of a shape memory material. For example, said shape memory material comprise nitinol.

The terminology "shape-memory material" refers to a material, for example an alloy, that remembers its pre-deformed shape and that when deformed returns to its pre-deformed shape when subject to a heat stress, for example heating, and it is not an isotherm process.

According to an embodiment, said at least one biasing device 24 comprises an elastic device and a shape memory material.

Preferably, said at least one biasing device 24 is embedded within the body of paddle 5. In this way the biasing device 24 is between the major surfaces 6, 7 of the paddle.

According to an embodiment, an envelope 40 is provided wrapping at least a portion of the paddle 5. Preferably, said envelope 40 wraps also a portion of the connection portion 13 of the lead 2. According to an embodiment, said envelope 40 forms a protective abutment portion 46 for the at least one paddle electrode 8 when in the transport configuration, so that the at least one paddle electrode 8 is recessed in respect of said protective abutment portion 46 of the envelope 40.

According to a preferred embodiment, said paddle 5 has a multi-layered structure comprising a plurality of layers. For example, said plurality of layers comprises: said conductive track 17 and/said at least one paddle electrode 8, a polymeric substrate 25 or carrier 25, and preferably said envelope 40.

According to a preferred embodiment, said paddle 5 is in form of a multilayered thin film.

According to a preferred embodiment, said paddle 5 is made of a flexible polymeric substrate 25 with embedded metal material forming said at least one conductive track 17 and/or said paddle electrode 8. According to an embodiment, said embedded metal material is in form of a plurality of nanoparticles arranged in such way to form electrical connection with said conductive surface 14 of the lead 2. In this way, the provision of said paddle fold 19 locally increases the electrically conductive capability of said conductive tracks 17.

According to an embodiment, said embedded metal material is in form of a metal plate.

According to a general embodiment, it is provided an assembly 51 comprising at least one device 1 according to any one of the embodiments described above, and at least one control device 36.

Preferably, said control device 36 is associated to said proximal end 3 of the lead 2, so that is in electrical communication with the exposed surface 9 of the at least one paddle electrode 8, through said lead 2, said arched connection surface 14 of the lead, said conductive counter-surface 16 of the paddle 5 and said conductive track 17.

According to an embodiment, said control device 36 comprises at least one pulse generator 36. In this way, a stimulator assembly 51 for electrotherapy is provided. The pulse generator may be implantable.

According to an embodiment, said control device 36 comprises at least a memory 36, for storing information about the electrical activity of a living tissue 10. In this way, a recorder assembly 51 for electrophysiology is provided. The memory may be implantable.

Preferably, said control unit 36 comprises a case 55 and at least one port 56 to receive the proximal end 3 of the lead 2. An adapter 52 and a cabled connection to the control unit 36 may be provided for connecting said lead 2 with said control unit 36, for fitting the size of the proximal end 3 of the lead 2 with the size of the port 56.

According to a general embodiment, it is provided a kit 30 comprising at least one device 1 according to any one of the embodiments described above, and a percutaneous delivery system 27 comprising at least one hollow body 28.

Advantageously, said hollow body 28 houses said at least one device 1 when in transport configuration.

According to an embodiment, said hollow body 28 is a longitudinally hollow body 28 defining a longitudinal cavity and comprising a proximal mouth 48 and a distal mouth 47.

According to an embodiment, said percutaneous delivery system 27 comprises a sheath 49, and said sheath 49 defines said hollow body 28.

According to an embodiment, said percutaneous delivery system 27 comprises a percutaneous needle 50, and said percutaneous needle 50 defines said hollow body 28.

According to an embodiment, said percutaneous delivery system 27 comprises also a guiding steerable stylet received inside the longitudinal cavity 18 of the lead 2. Preferably, the device 1 comprises a distal free end portion 58 free from contact with said paddle 5, said free end portion 58 delimiting a distal portion of said longitudinal cavity 18. In this way, the manoeuvrability of the device 1 is enhanced.

According to an embodiment, said percutaneous delivery system 27 comprises also a delivery catheter having a proximal end and a distal end, wherein the device 1 is near the distal end of the catheter. Preferably, the proximal end of the catheter is associated to a caterer handle designed to be hand held by a surgeon.

According to a preferred embodiment, said at least one paddle fold 19 defining a transversally folded portion 20 of the paddle 5 is contained inside the transversal size 29 of the hollow body 28 of the percutaneous delivery system 27. In this way, when the paddle 5 is folded fits the size 29 of the hollow body 28 of the percutaneous delivery system 27. For example, the size 29 of the hollow body 28 of the percutaneous delivery system 27 is about 14G.

According to a preferred embodiment, said hollow body 28 acts as constraining body for the paddle 5 constraining the paddle 5 in the transport configuration. In this way, the paddle 5 abuts against the hollow body.

When the paddle 5 is extracted from the delivery system 27, for example by means of retraction of the sheath 49, the paddle wings 21 modify their angular position with respect to said lead 2, thus increasing the transverse or radial encumber 12 thereof. Void portions 59 may be provided inside the delivery system when the paddle 5 is in transport configuration.

Figure 15:
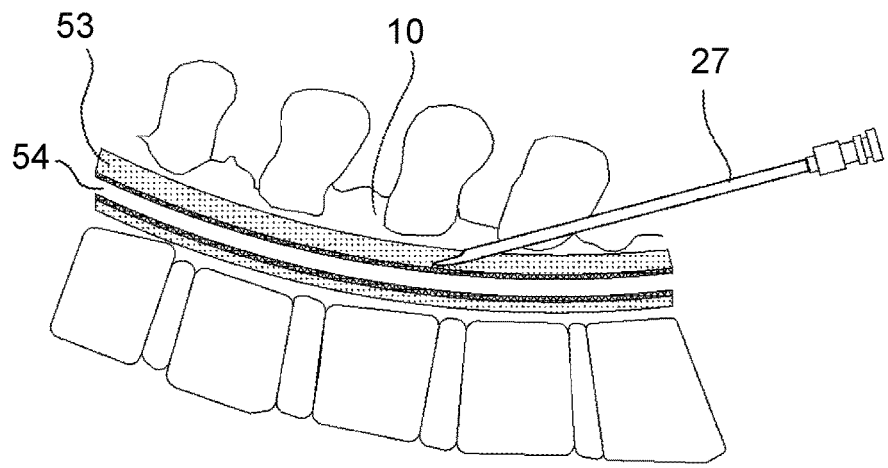
FIG. 15 shows diagrammatically a target living anatomy.
Figure 16:
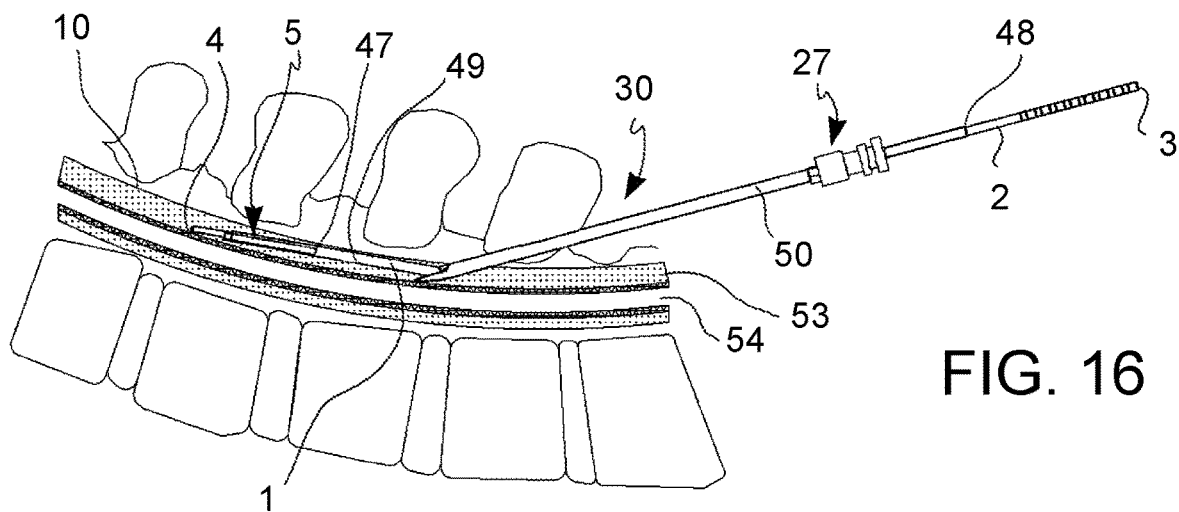
FIG. 16 shows a device, according to an embodiment, during implantation in the target living anatomy of FIG. 15.
Figure 17:
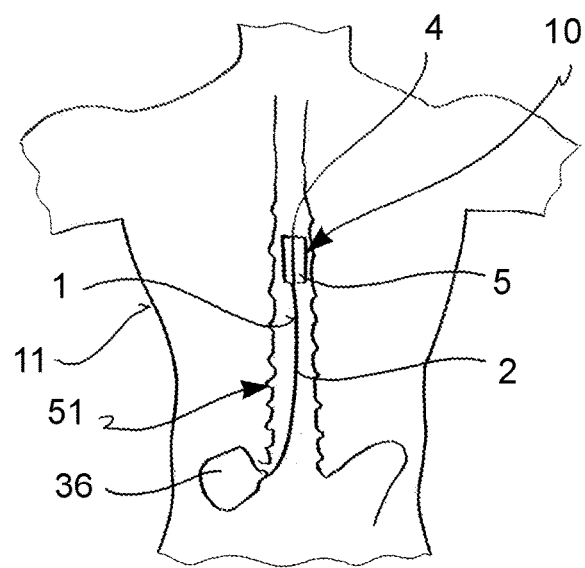
FIG. 17 shows diagrammatically an assembly comprising a device, according to an embodiment, when implanted in a target living anatomy.
Figure 18:
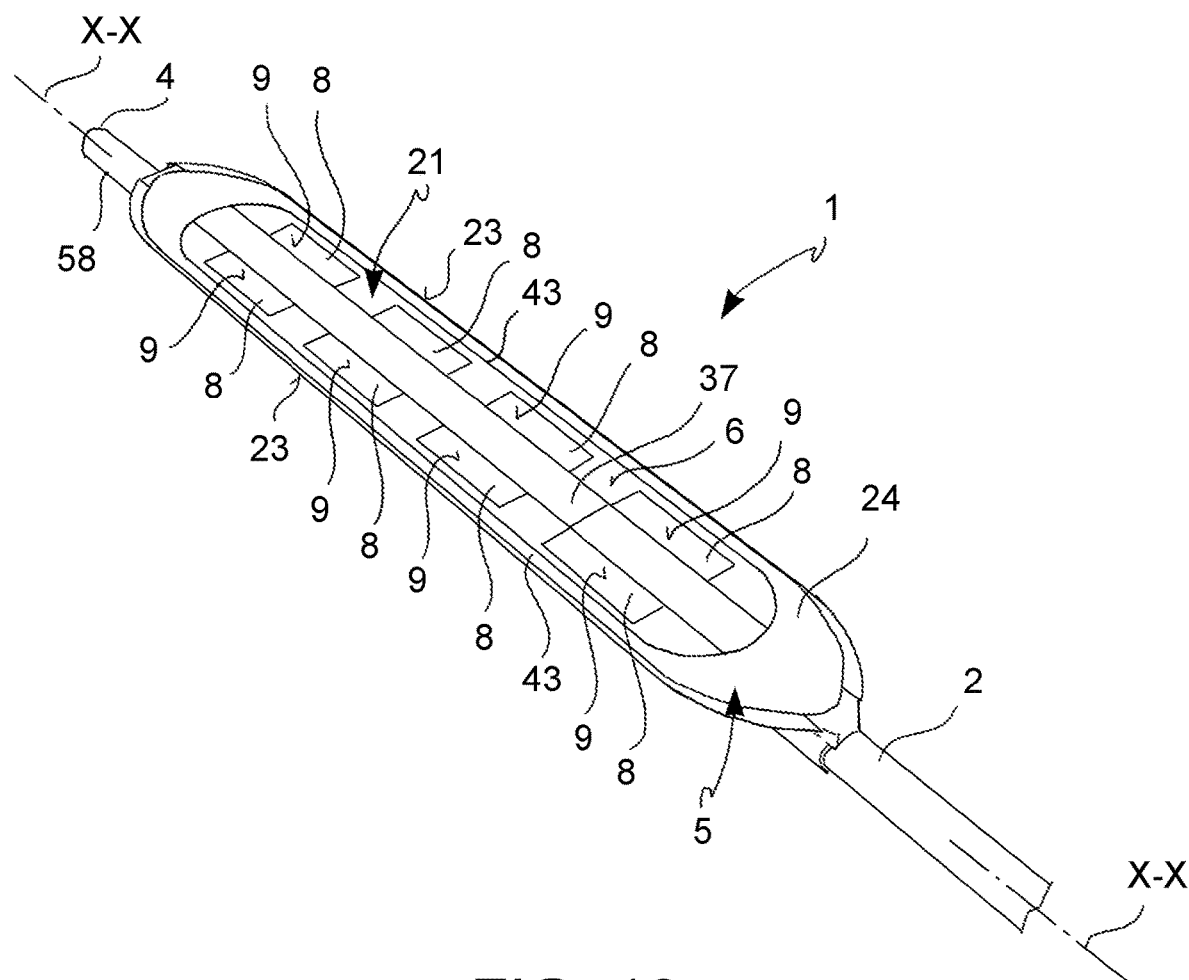
FIG. 18 shows a perspective view of a device, according to an embodiment as described herein.

According to a preferred embodiment as shown for example in FIGS. 15, 16 and 17, and with particular reference to spinal cord stimulation applications, said device 1 comprising a paddle 5 as described above, allows for percutaneous implantation within the epidural space 53 of a target living anatomy 10, preferably a human target living anatomy 10, without for that reason limiting the maximum transversal size of the paddle 5. Therefore, it is possible to apply localized and directional electrical stimulation to the spinal cord 54, thanks to a suitably designed disposition of the electrodes 8 and the orientation of the paddle wings 21, and at the same time the implantation is achieved through mininvasive surgery.

A method of percutaneous implant of a device 1 will be described in the following.

The method of percutaneous implant comprises the steps of: providing a device 1, according to any one of the embodiments described above; transporting the device 1 near a target living anatomy 48; delivering the device 1 into a target living anatomy 10 inside a patient body 11.

The method of percutaneous implant comprises the step of unloading the device 1.

Preferably, this step is carried out by means of gradually longitudinally exit the device 1 from the percutaneous delivery system 27, in such way that a first portion of the paddle 5 is already in the implant configuration while a second portion of the paddle 5, is still in the transport configuration within an hollow body 28 of the delivery system 27.

Then, the method of percutaneous implant comprises the further step of increasing, preferably gradually increasing, the transverse or radial encumber 12 of said device 1.

Thanks to the features described above, provided either separately or jointly in particular embodiments, it is possible to respond to the above-cited drawbacks and to provide the above-cited advantages, and in particular: (i) it is provided an implantable paddle lead for electrotherapy and electrophysiology that allow minimally invasive procedure for implantation and/or for explanation; (ii) the interconnection between a thin stretchable polymer with embedded conductive stretchable metal lines and electrode with a cylindrical lead, allow to transform a multi-directional stimulation given by a cylindrical lead in a directional stimulation of a paddle electrode; (iii) the arched portions offer a stretched side and an opposite compressed side at the area of interconnection between paddle and lead; (iv) the provision of a "omega"-like shape when the paddle is in the transport configuration allows to save space during transport when compared to other configurations because it avoids to provide welding points and/or cables; (v) the electrical connection of the cylindrical lead and metal lines is such that it allows a larger area of contact with respect of known solutions, which decreases resistance and decreases manufacturing challenges during assembly; (vi) therefore, a lower delivery sheath diameter over paddle width ratio is achieved in respect of known solutions; (vii) furthermore, the "omega"-like shape of the transport configuration of the paddle allows the folding of the paddle around a cylindrical lead, thus permitting the insertion in a catheter sheath that brings the paddle in the target position; (viii) the paddle may have eight electrode divided in two columns of four, or it can have more electrodes, for example two columns of eight, while can be introduced percutaneously; (ix) when in position the paddle is opened by the extraction of the sheath; (x) the action needed to open the paddle may be given by an embedded spring within the paddle body; (xi) the cylindrical lead has a lumen dedicated to the stylet to allow insertion of straight or bended stylet to steer the catheter and the device inside the epidural space for spinal cord stimulation and/or recording; (xii) if the proximal lead end is smaller, to save space and keep needle dimension smaller, an adapter or a special cable with the two extremities with different dimension may be provided for; (xiii) the provision of a needle with rounded edges at its distal mouth avoids to damage the lead and the paddle; (xiv) it is possible to convert a cylindrical multi-directional lead electrode into a wide-area directional lead, having a compact design that minimize the volume of space needed for the interconnection of the lead to the paddle electrodes; (xv) it is provided a paddle having a flat part that can be folded around the cylindrical lead, to save space for the insertion through minimally invasive tools like catheters, sheaths and/or cannula devices Those skilled in art may make many changes and adaptations to the embodiments described above or may replace elements with others that are functionally equivalent in order to satisfy contingent needs without however departing from the scope of the appended claims.

LIST OF REFERENCES

1 Device
2 Lead
3 Proximal end of the lead
4 Distal end of the lead
5 Paddle
6 First major surface of the paddle
7 Second major surface of the paddle
8 Paddle electrode
9 Exposed surface of the paddle electrode
10 Living anatomy
11 Patient body
12 Transversal or radial encumber
13 Connection portion of the lead
14 Arched conductive surface of the connection portion of the lead
15 Counter-connection portion of the paddle
16 Conductive counter-surface of the paddle
17 Conductive track
18 Longitudinal cavity
19 Paddle fold
20 Folded portion of the paddle
21 Paddle wing, or wing
22 Transversal edge of the paddle
23 Free end of the wing
24 Biasing device
25 Polymeric substrate
27 Percutaneous delivery system
28 Hollow body
29 Cavity size
30 Kit
31 Longitudinal size of the paddle
32 Width of the paddle
33 Thickness of the paddle
35 Electrical contacts of the proximal end of the lead
36 Control unit
37 Glue
38 Clip
39 Flex
40 Envelope
41 First portion of the major surface
42 Second portion of the major surface
43 Elongated element of the biasing device
44 Hole or window of the biasing device
45 Stiffening element of the biasing device
46 Protective abutment portion
47 Distal mouth of the delivery system
48 Proximal mouth of the delivery system
49 Sheath
50 Needle
51 Assembly
52 Adapter
53 Epidural space
54 Spinal cord
55 Case of the control unit
56 Port of the control unit
57 Electrically insulant portion of the of the connection portion of the lead
58 Distal free end of the device
59 Void portion
R1 First concavity
R2 Second concavity
X-X Longitudinal direction
Y-Y Transversal direction or radial direction

The invention claimed is:

1. A device (1) for electrotherapy and/or electrophysiology comprising:
at least one lead (2) having an elongated lead body extending along a longitudinal direction (X-X) and comprising a proximal end (3) and a distal end (4); and
at least one paddle (5) having a paddle body comprising two opposite major surfaces (6, 7) defining a paddle thickness (33) there between;
and wherein:
said paddle (5) comprising at least one paddle electrode (8) having an exposed surface (9) designed to come into electrical contact with a living anatomy (10) inside a patient's body (11);
said paddle (5) is suitable to modify the transverse encumber (12) thereof, so that to assume at least one transport configuration and at least one operative configuration, wherein the transverse encumber (12) of the paddle (5) when in said at least one transport configuration is less than the transverse encumber (12) of the same paddle (5) when in said at least one operative configuration;
and wherein:
said lead (2) comprising a connection portion (13) near the distal end (4) thereof; and characterised in that
said connection portion (13) of the lead (2) comprises at least one arched electrically conductive surface (14); and
said paddle (5) comprises at least one counter-connection portion (15) comprising at least one arched electrically conductive counter-surface (16) in direct contact with said at least one conductive surface (14) of the connection portion (13) of the lead (2), so that said at least one counter-connection portion (15) of the paddle (5) has a transversally arched shape defining a first concavity (R1) facing towards said connection portion (13) of the lead (2), wherein said connection portion (13) of the lead (2) has a cylindrical shape and said counter-connection portion (15) of the paddle (5) embraces at least a portion of said cylindrical connection portion (13) of the lead (2);
said at least one conductive counter-surface (16) of the paddle (5) is in electric communication with said paddle electrode (8) through at least one conductive track (17) extending within the body of paddle (5) in such way that said proximal end (3) of the lead (2) is in electrical communication with said exposed surface (9) of the at least one paddle electrode (8).

2. The device (1) according to claim 1, wherein said paddle (5) comprises at least one paddle fold (19) defining at least one transversally folded portion (20) of the paddle (5) comprising said at least one paddle fold (19); and/or wherein
said at least one transversally folded portion (20) of the paddle (5) defines a second concavity (R2) opposite to said first concavity (R1).

3. The device (1) according to claim 2, wherein said paddle (5) comprises at least one paddle transversal edge (22) delimiting the width of said major surfaces (6, 7), and wherein said at least one paddle fold (19) is located between said counter-connection portion (15) and said transversal edge (22) of the paddle (5), defining a paddle wing (21) comprising a free end (23) and at least a portion of said at least one paddle electrode (8).

4. The device (1) according to claim 2, wherein said at least one paddle fold (19) defining at least one transversally folded portion (20) of the paddle (5) is provided both when the paddle (5) is in the transport configuration and when the paddle (5) is in the operative configuration.

5. The device (1) according to claim 1, wherein said paddle (5) comprises two opposite paddle folds (19) opposite with respect to said counter-connection portion (15) of the paddle (5) defining at least two opposite paddle wings (21) each having a free end.

6. The device (1) according to claim 1, comprising at least one biasing device (24) biasing said paddle (5) towards said operative configuration; and/or wherein said at least one biasing device (24) comprises at least one elastic element, made of elastic and/or a super-elastic material; and/or wherein said at least one biasing device (24) comprises at least one shape memory element made of a shape memory material; and/or wherein said at least one biasing device (24) is embedded within the paddle (5).

7. The device (1) according to claim 1, wherein said paddle (5) has a multi-layered structure; and/or wherein said paddle (5) is made of a polymeric substrate (25) with embedded and/or deposited thin film of metal material forming said at least one conductive track (17) and/or said paddle electrode (8); and/or wherein said embedded metal material is in form of a plurality of nanoparticles arranged in such way to form electrical connection with said conductive surface (14) of the lead (2); and/or wherein said embedded metal material is in form of a metal plate.

8. The device (1) according to claim 1 further comprising:

a distal free end portion (58) free from contact with said paddle (5), said free end portion (58) delimiting a distal portion of said longitudinal cavity (18) a longitudinal cavity (18) for hosting a guiding stylet.

9. A kit (30) comprising:

at least one device (1) according to claim 1 and a percutaneous delivery system (27) comprising at least one hollow body (28), wherein said hollow body (28) houses said at least one device (1) when in transport configuration.

10. The kit (30) according to claim 9, wherein said paddle (5) of the device (1) comprises at least one fold defining a transversally folded segment of the paddle (5) that fits inside the hollow body (28) of the percutaneous delivery system (27).

11. The kit (30) according to claim 9, wherein said hollow body (28) acts as constraining body for the paddle (5) constraining the paddle (5) in the transport configuration.

12. An assembly (51) comprising:

at least one device (1) according to claim 1 and at least one control unit (36), wherein said assembly (51) is a stimulator for electrotherapy and/or a recorder for electrophysiology.

* * * * *